(12) United States Patent
Chiu et al.

(10) Patent No.: US 9,663,628 B2
(45) Date of Patent: May 30, 2017

(54) STABILIZED MONOMER DISPERSION CONTAINING INORGANIC OXIDE NANOPARTICLES WITH HIGH REFRACTIVE INDEX AND ITS PREPARATION

(71) Applicant: National Taiwan University, Taipei (TW)

(72) Inventors: Wen-Yen Chiu, Taipei (TW); I-Ann Lei, Taichung (TW); Dai-Fu Lai, New Taipei (TW); Wen-Chang Chen, Taipei (TW); Yang-Yen Yu, Taipei (TW); Guey-Sheng Liou, Taipei (TW); Trong-Ming Don, Taipei (TW)

(73) Assignee: National Taiwan University, Taipei (TW)

( * ) Notice: Subject to any disclaimer, the term of this patent is extended or adjusted under 35 U.S.C. 154(b) by 201 days.

(21) Appl. No.: 14/735,491

(22) Filed: Jun. 10, 2015

(65) Prior Publication Data

US 2015/0284529 A1 Oct. 8, 2015

Related U.S. Application Data

(62) Division of application No. 13/358,027, filed on Jan. 25, 2012, now abandoned.

(30) Foreign Application Priority Data

| Apr. 18, 2011 | (TW) | ............................... 100113347 A |
| Dec. 9, 2011 | (TW) | ............................... 100145476 A |

(51) Int. Cl.
*B01J 31/00* (2006.01)
*C08K 3/22* (2006.01)
(Continued)

(52) U.S. Cl.
CPC ................ *C08K 3/22* (2013.01); *B82Y 30/00* (2013.01); *C07C 15/02* (2013.01); *C07C 31/202* (2013.01);
(Continued)

(58) Field of Classification Search
CPC ................................... C08F 2/44; B82Y 20/00
(Continued)

(56) References Cited

U.S. PATENT DOCUMENTS

| 2005/0168799 A1 | 8/2005 | Whitesides et al. |
| 2007/0062445 A1 | 3/2007 | Kodou et al. |

(Continued)

FOREIGN PATENT DOCUMENTS

JP 2009-024068 * 2/2009 ............... C08F 2/44

*Primary Examiner* — Khanh Tuan Nguyen
(74) *Attorney, Agent, or Firm* — Muncy, Geissler, Olds & Lowe, P.C.

(57) ABSTRACT

The present invention relates to a stabilized monomer dispersion containing inorganic oxide nanoparticles with high refractive index in which the refractive index of the inorganic oxide nanoparticles is greater than 1.65 and the average particle size of the high refractive inorganic oxide nanoparticles ranges from 1 to 100 nm and its content is in a range of from 1.0% by weight to 10.0% by weight based on the total weight of the monomer dispersion. The present invention also relates to a process for preparing the stabilized monomer dispersion containing high refractive inorganic oxide nanoparticles.

7 Claims, 6 Drawing Sheets

(51) Int. Cl.
  *B82Y 30/00*    (2011.01)
  *C08F 20/14*    (2006.01)
  *C09C 1/36*     (2006.01)
  *C09C 3/10*     (2006.01)
  *H01B 1/12*     (2006.01)
  *C07C 15/02*    (2006.01)
  *C07C 31/20*    (2006.01)
  *C07C 69/54*    (2006.01)
  *C07C 211/46*   (2006.01)
  *C07D 303/16*   (2006.01)
  *C08K 5/09*     (2006.01)
  *C08K 5/56*     (2006.01)
  *G02B 6/12*     (2006.01)

(52) U.S. Cl.
  CPC ............ *C07C 69/54* (2013.01); *C07C 211/46* (2013.01); *C07D 303/16* (2013.01); *C08F 20/14* (2013.01); *C08K 5/09* (2013.01); *C08K 5/56* (2013.01); *C09C 1/3676* (2013.01); *C09C 3/10* (2013.01); *H01B 1/124* (2013.01); *C01P 2002/88* (2013.01); *C01P 2004/52* (2013.01); *C01P 2004/64* (2013.01); *C08K 2003/2213* (2013.01); *C08K 2003/2241* (2013.01); *C08K 2003/2244* (2013.01); *G02B 2006/12071* (2013.01)

(58) Field of Classification Search
  USPC .......................................................... 502/159
  See application file for complete search history.

(56) References Cited

U.S. PATENT DOCUMENTS

2007/0146887 A1    6/2007   Ikeda et al.
2011/0143923 A1*   6/2011   Bette ................. B82Y 20/00
                                                502/159

* cited by examiner

STABILIZED MONOMER DISPERSION CONTAINING INORGANIC OXIDE NANOPARTICLES WITH HIGH REFRACTIVE INDEX AND ITS PREPARATION

CROSS-REFERENCE TO RELATED APPLICATIONS

This application is a Divisional of co-pending application Ser. No. 13/358,027 filed on Jan. 25, 2012, for which priority is claimed under 35 U.S.C. §120; and this application claims priority of Application No. 100113347 filed in Taiwan on Apr. 18, 2011, and Application No. 100145476 filed in Taiwan on Dec. 9, 2011, under 35 U.S.C. §119, the entire contents of all of which are hereby incorporated by reference.

BACKGROUND OF THE INVENTION

1. Technical Field

The present invention relates to a stabilized monomer dispersion containing inorganic oxide nanoparticles and a process for preparing the same. More particularly, the present invention relates to a stabilized monomer dispersion containing inorganic oxide nanoparticles with high refractive index and a process for preparing the same.

2. Description of Related Art

It is well known that some inorganic oxides such as titania (also known as titanium dioxide), zirconia (also known as zirconium dioxide), and ceria (also known as cerium dioxide) exhibit high refractive index. Therefore if such high refractive inorganic oxides were modified with organics, they can be formed into transparent and high refractive optical films and thus increase their utility. Such inorganic dioxides are now briefly discussed as follows.

Titanium dioxide ($TiO_2$), also known as titanium white, exists three crystal forms, namely anatase, rutile, and brookite. Titanium dioxide is a white pigment which has been used in significant amount in most applications. It can also be used as an additive in cosmetic for absorbing ultraviolet light and thus providing sun-screen effect. Among them, the anatase also possesses a photo-catalytic property for rendering deodorization, disinfection, decontamination, and demisting effects.

As to the zirconium dioxide ($ZrO_2$), it is a major oxide of zirconium and is normally a white, odorless, and tasteless crystal and is hardly soluble in water, hydrochloric acid, or dilute sulfuric acid. It exists in the nature as a baddeleyite, which is a monoclinic crystalline structure. Since zirconium dioxide is chemically inactive and has a high melting point, high resistivity, high refractive index, and low thermal expansion coefficient, it is an important high heat-resistant material, insulating ceramic material, and ceramic opacifier.

Cerium dioxide ($CeO_2$) is a white or light yellow solid and is hardly soluble in water or common acids and bases solution. Recently, cerium dioxide powder is of great importance in the catalytic industries, functioning mainly as an oxidative catalyst or as a catalyst support. For example, cerium dioxide can be used in a three-way catalyst (TWC) converter catalyzing the oxidation of carbon monoxide, nitrogen oxides, hydrocarbons, etc. exhausted from vehicles and thereby reduce air pollution caused by such exhaust.

The above-mentioned high refractive inorganic oxides are usually prepared by a sol-gel process, which is a general process of conversion between two physicochemical states. More specifically, the term "sol" refers to colloidal particles which are evenly dispersed in a liquid and remained active therein. The colloidal particles have a particle size ranging from 1 to 100 nm and exhibit Brownian motion while being suspended in the liquid. As to the gel, it is formed by evaporating solvent in the sol continuously to increase the concentration of the colloid particles so that the particles collide with each other and re-combine to form a multi-dimensional cross-linked structure, which molecular weight would be infinitely increased and could be shaped as desired.

In the sol-gel preparation process, the precursor of inorganic oxide (e.g., titanium alkoxide or zirconium alkoxide, etc.,) reacts in an alcohol solvent having the same number of carbon atoms as the alkyl group of the alkoxide in the precursor so as to prevent the alkoxy of the alkoxide from inter-reacting with the alkyl group of the alcohol. Then, condensation and hydrolysis are carried out to form a sol-gel oxide. The sol-gel oxide is subsequently mixed with other materials and subjected to cross-linking after evaporating the solvent to obtain the desired inorganic oxides.

However, such a sol-gel process described above is complicated since an inorganic oxide nano-material must be prepared in advance, and then mixed with other materials to be reacted.

After conducting intensively investigation on the preparation processes of inorganic oxide nanoparticles, the inventors of the present application found that if a dispersion containing stably suspended inorganic oxide nanoparticles can be prepared directly in a reactive monomer, then a polymer material having the desired thermal stability can be easily obtained upon polymerizing the reactive monomer suspended with the inorganic oxide nanoparticles, thus completed the present invention.

SUMMARY OF THE INVENTION

The present invention relates to a stabilized monomer dispersion containing inorganic oxide nanoparticles with high refractive index, wherein the refractive index of the inorganic oxide nanoparticles is greater than 1.65, the average particle size of the inorganic oxide nanoparticles is in a range of from 1 to 100 nm and its content is in a range of from 1.0% by weight to 10.0% by weight based on the total weight of the monomer dispersion.

The stabilized monomer dispersion containing inorganic oxide nanoparticles with high refractive index of the present invention can be further polymerized in the presence of a polymerization initiator to form a polymer material. The polymer material thus produced can be formed into a film by a coating method and thus to be applied to an optical device.

The present invention also relates to a process for preparing a stabilized monomer dispersion containing inorganic oxide nanoparticles with high refractive index, wherein the inorganic oxide is selected from titanium dioxide, zirconium dioxide, and cerium dioxide, which process includes the steps of condensing and then hydrolyzing alkoxide precursors corresponding to the oxides in a reactive monomer which serves as a solvent, in the presence of a chelating agent and water, at a temperature ranging from 0 to 50° C. to produce a dispersion consisting of the reactive monomer and the nanoparticles of the inorganic oxides suspended therein, wherein, the equivalent ratio of the water to the alkoxide, i.e., the equivalent ratio of water/alkoxide, is equal to or less than 3, and the equivalent ratio of the chelating agent to the alkoxide is 2 or above, preferably in the range from 2 to 10.

DETAILED DESCRIPTION OF THE INVENTION

Figure 1:
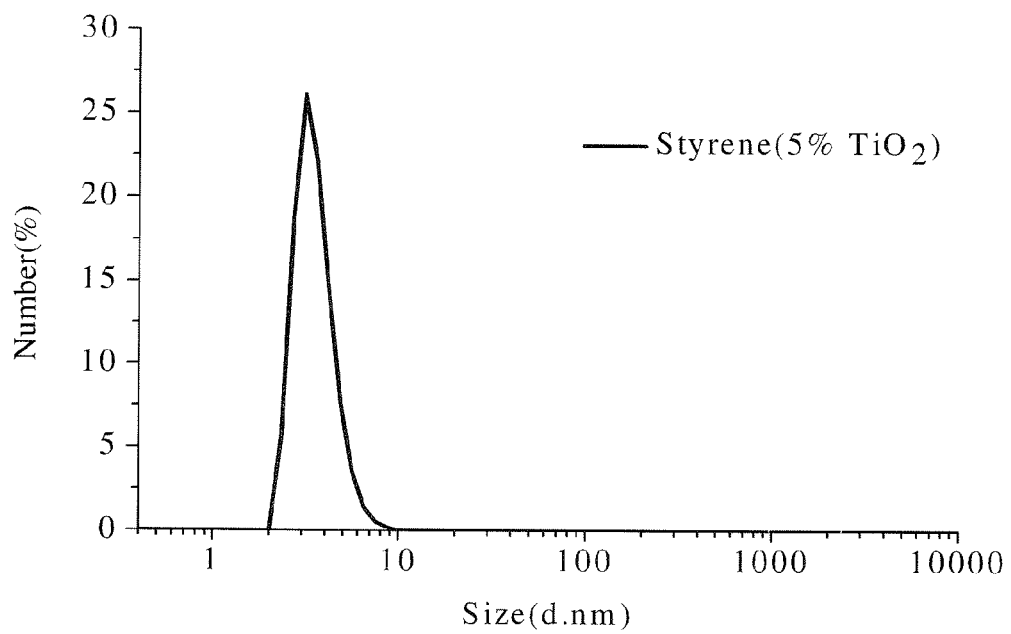
FIG. 1 is a graph showing the particle size distribution of the titanium dioxide nanoparticles dispersed in the monomer dispersion prepared in Example 1.

The present invention relates to a stabilized monomer dispersion containing inorganic oxide nanoparticles with high refractive index, wherein the refractive index of the inorganic oxide nanoparticles is greater than 1.65, the average particle size of the inorganic oxide nanoparticles is in a range of from 1 to 100 nm and its amount is in a range of from 1.0% by weight to 10.0% by weight based on the total weight of the monomer dispersion.

As the term "refractive index" used herein refers to the ratio of the speed of light travelling in vacuum relative to the speed of light travelling in a medium (i.e., the inorganic oxide). The term "high refractive index" used herein refers to the refractive index greater than 1.65, preferably greater than 2.00. The term "(meth)acrylic" used herein means acrylic or methacrylic or both. The term "stabilized" used herein means that the inorganic oxide would not grow or aggregate to form a particle having a particle size exceeding 100 nm when it is stored in ambient temperature. In the present invention, the inorganic oxide nanoparticles having a high refractive index are selected from, but not limited to, titanium dioxide, which refractive index is about from 2.20 to 2.52; zirconium dioxide, which refractive index is about from 2.15 to 2.20; and cerium dioxide, which refractive index is about 2.18.

In the stabilized monomer dispersion containing inorganic oxide nanoparticles with high refractive index of the present invention, the average particle size of the inorganic oxide nanoparticles is in a range of from 1 to 100 nm, preferably from 2 to 50 nm, more preferably from 10 to 40 nm. If the average particle size is greater than 100 nm, the film prepared from the present dispersion will become non-transparency in the visible light and therefore could not be used in applications where transparency is required and is not preferred.

In the stabilized monomer dispersion containing inorganic oxide nanoparticles with high refractive index of the present invention, the amount of the inorganic oxide nanoparticles is in a range of from 1.0% by weight to 10.0% by weight, preferably from 1.0% by weight to 8.0% by weight, more preferably from 2.0% by weight to 5.0% by weight, based on the total weight of the monomer dispersion. If the amount of the inorganic oxide particles is greater than 10.0% by weight, the distance between particles will be so close so that they tend to collide with each other and cross-link continuously, resulting in the inorganic oxide particles growing to particles having average particle size exceeding the range set forth above, which is undesirable.

The present invention also relates to a process for preparing a stabilized monomer dispersion containing inorganic oxide nanoparticles with high refractive index, wherein the inorganic oxide is selected from titanium dioxide, zirconium dioxide, and cerium dioxide, which process includes the steps of condensing and then hydrolyzing alkoxide precursors corresponding to the oxides in a reactive monomer (which serves as a solvent) in the presence of a chelating agent and water, at a temperature of from 0 to 50° C., to produce a dispersion consisting the reactive monomer and nanoparticles of the inorganic oxides suspended therein. In the present process, the equivalent ratio of the water to the alkoxide, i.e., the equivalent ratio of water/alkoxide, is equal to or less than 3, preferably 2. The equivalent ratio of the chelating agent to the alkoxide is at least 2, preferably in the range of from 2 to 10.

The reactive monomer for use in the process of the present invention can be any monomer which is liquid at the temperature which the present process is performed, i.e., at the temperate of from 0 to 50° C., preferably from 10 to 30° C. For example, the monomers used in the present invention include monomers having an ethylenic functional group, electrically conductive monomers, or polycondensation reactive monomers. Such monomers can be used alone, or in a mixture of at least two different types of monomer, as long as that the different types of monomer would not react with each other nor resulting in any adverse effects on the desired end use.

Examples of monomers with an ethylenic functional group are styrenic monomers and (meth)acrylic monomers.

For instance, the styrenic monomers include styrene and α-methyl styrene, etc. and (meth)acrylic monomers include 2-hydroxyethyl acrylate, 2-hydroxyethyl methacrylate, glycidyl acrylate, glycidyl methacrylate, acrylic acid, methacrylic acid, methyl acrylate, methyl methacrylate, allyl acrylate, allyl methacrylate, vinyl acetate, ethylene, propylene, butylene, and isobutylene, etc.

Examples of electrically conductive monomers are aniline, 3,4-ethylenedioxy thiophene (EDOT), and pyrrole, etc.

Examples of polycondensation reactive monomers are ethylene glycol and propylene glycol, etc.

The monomer(s) is(are) selected depending on the desired end use. For example, where electrically conductive films are required, an electrically conductive monomer may be selected as the solvent in the process of the present invention.

The alkoxide used in the process for preparing a stabilized monomer dispersion containing inorganic oxide nanoparticles with high refractive index of the present invention is represented by $X(OR)_4$, where R's are the same or different and represent a straight or branched alkyl group having 1 to 8 carbon atoms, and X represents Ti, Zr, or Ce. Examples of the alkoxides include titanium tetramethoxide, titanium tetraethoxide, titanium tetrapropoxide, titanium tetraisopropoxide, titanium tetrabutoxide, titanium tetraisobutoxide, tetra(2-ethylhexyloxy) titanium, zirconium tetramethoxide, zirconium tetraethoxide, zirconium tetrapropoxide, zirconium tetraisopropoxide, zirconium tetrabutoxide, zirconium tetraisobutoxide, tetra(2-ethylhexyloxy) zirconium, cerium tetramethoxide, cerium tetraethoxide, and cerium tetrapropoxide, etc.

In the process for preparing a stabilized monomer dispersion containing inorganic oxide nanoparticles with high refractive index of the present invention, the chelating agent is used for chelating the hydroxyl group of the inorganic oxide so that the inorganic oxide will not further collide to keep growing and eventually become gelated. The chelating agent which can be used is a compound having a carboxyl (—COOH) functional group, such as acetic acid and citric acid, etc. If the monomer serving as the solvent possesses a carboxyl functional group, such as acrylic acid, the monomer itself can also function as the chelating agent.

A stabilized monomer dispersion containing inorganic oxide nanoparticles with high refractive index as prepared by the process of the present invention can further undergo polymerization in the presence of a photopolymerization initiator or a thermopolymerization initiator, so that a desired organic-inorganic hybrid polymer material (hereafter sometimes briefly refer to "the polymer material") such as a polymer film can be made for the intended use. The polymerization can be carried out by polymerization methods well known in the art, such as thermopolymerization, photopolymerization, solution polymerization, emulsion polymerization, and bulk polymerization, etc, depending on the type of monomer in use. The conditions for the polymerization reaction are also well known in the art and therefore will not be detailed herein.

In the stabilized monomer dispersion containing inorganic oxide nanoparticles with high refractive index as prepared by the process of the present invention, the nanoparticles of the inorganic oxide are evenly and stably dispersed. Therefore, the stabilized monomer dispersion containing the inorganic oxide nanoparticles could further subject to polymerization in the presence of polymerization initiator and give an organic-inorganic hybrid polymer material of excellent thermal stability. When the polymer material is formed into a film, the resultant film has excellent thermal stability and is transparent, high refractive, and hence is suitable used in optical applications.

The polymerization initiator for initiating polymerization of the stabilized monomer dispersion of the present invention can be a photopolymerization initiator, an azo compound such as azobisisobutyronitrile (AIBN), a redox initiator such as iron (III) p-toluenesulfonate hexahydrate, or a peroxide such as a benzoyl peroxide (BPO), etc. As the aforementioned polymerization initiators are well known in the art, and their use amounts can be readily determined according to the type of monomer to be polymerized, further details are omitted herein.

The polymer material obtained by polymerization of the stabilized monomer dispersion of the present invention has wide applicability due to its high transparency, high refractive index, thermal stability, and ability to absorb ultraviolet (UV) light. For example, it can be made into a high refractive transparent film for use in optical applications. Alternatively, if an electrically conductive monomer is used as the suspension medium, the resultant polymer material will be electrically conductive, transparent, high refractive, and hence be applicable to the field of semiconductor. Furthermore, the polymer material can also be formed into high refractive composite latex particles.

Hereinafter, the present invention will be described in more detail with reference to the following embodiments, which are provided by way of example only and should not be construed as limiting the scope thereof.

First of all, the methods for determining the physical properties of the stabilized monomer dispersions produced in the following embodiments and the physical properties of resultant products in subsequent applications are described below.

1. Particle Size Distribution Analysis of Inorganic Oxide Nanoparticles:

A monomer dispersion containing inorganic oxide nanoparticles is diluted to one fifth concentration of the original by adding the same monomer used as the medium (solvent) in the dispersion. Then, a dynamic light scattering (DLS) apparatus is used to determine the particle size distribution of the inorganic oxide nanoparticles in the monomer dispersion.

2. Determination of Thermal Stability:

The polymer material obtained by polymerization, of a stabilized monomer dispersion containing inorganic oxide nanoparticles in the presence of a polymerization initiator is dried in an oven at 110° C. for 24 hours. Then, the polymer material is heated by a thermogravimetric analyzer (TGA, Perkin Elmer TGA7) at a temperature increasing from 110° C. to 800° C. at 10° C./min for the TGA to determine the thermal stability of the polymer material.

3. Determination of Refractive Index and Transmittance:

A stabilized monomer dispersion containing inorganic oxide nanoparticles is spin-coated on a glass substrate to polymerize and form a film on the glass. The film is dried at room temperature to form a transparent optical film. The refractive index and thickness of the film are measured by using an ellipseometer (Sopra ges-51) at an incident wavelength ranging from 250 nm to 800 nm. Then, a transmittance of the film is measured by using UV-Vis (HeλIOSγ) at an incident wavelength ranging from 300 nm to 800 nm.

4. Determination of Electrical Conductivity:

In case of that the monomer of a stabilized monomer dispersion containing inorganic oxide nanoparticles is an electrically conductive monomer, the stabilized monomer dispersion is spin-coated on a glass plate in the presence of a polymerization initiator such that a film is formed while the monomer dispersion is polymerized in situ. The film is then coated with two stripes made from silver paste as electrodes and is dried in an oven at 110° C. The electrical resistance|$Z_m$|and the thickness of the film is measured by using an Volt-Ohm-Milliammeter (VOM) and a profilometer (Surfcorder ET3000), respectively, and electrical conductivity ($K_m$) of the film is calculated as follows:

$$K_m = \frac{d_m}{A \times |Z_m|}$$

wherein $d_m$ is the distance between the two silver paste stripes, $Z_m$ is the measured electrical resistance, and A is to the product of the silver paste length by the thickness of the electrically conductive film.

Example 1

In a mixture of 5.3 g styrene monomer and 1.53 g titanium tetraisopropoxide, 0.647 g of acetic acid as the chelating agent (with the molar equivalent ratio of acetic acid to titanium tetraisopropoxide being 2) and 0.2 g of water (with the molar equivalent ratio of water to titanium tetraisopropoxide being 2) were added. The resultant mixture was stirred at a temperature of 25° C. to hydrolyze titanium tetraisopropoxide to give a transparent clear solution which was a styrene monomer dispersion containing 5% by weight of titanium dioxide. The particle size distribution of the titanium dioxide particles of the styrene dispersion was measured with a DLS apparatus (Zetasizer nano ZS). The result showed that the particle size ranges from 2.0 to 9.0 nm and the particle size distribution graph was shown in FIG. 1.

Figure 2:
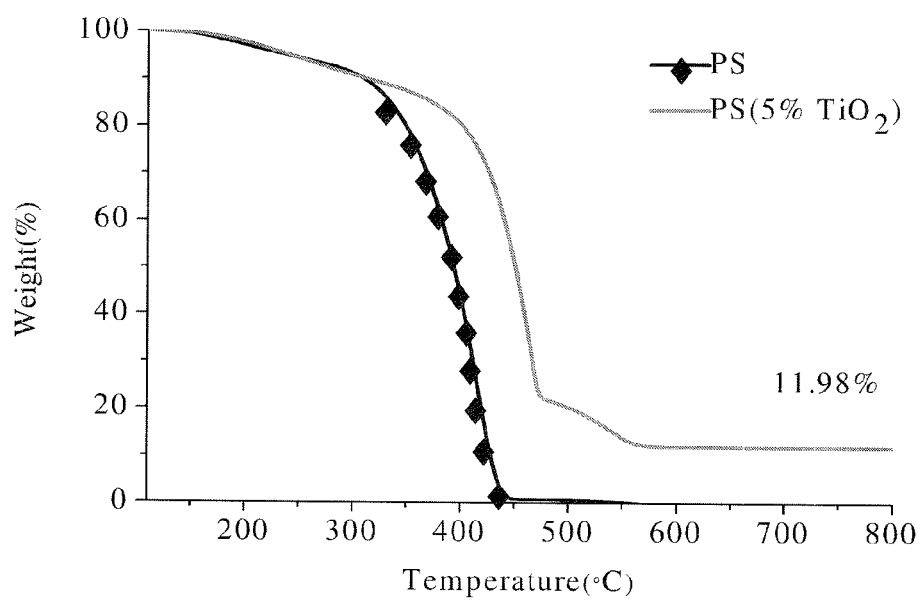
FIG. 2 is a graph showing the thermal analysis result of an organic-inorganic hybrid polymer material prepared in Example 1, in which the polymer material is obtained by polymerizing the monomer dispersion containing titanium dioxide nanoparticles.

Then, 0.02 g of azobisisobutyronitrile (as the polymerization initiator) was added into 2 g of the obtained styrene monomer dispersion containing 5% by weight of titanium dioxide particles, and thermopolymerization was performed at a temperature of 90° C. for 3 hours to obtain a polystyrene polymer material containing titanium dioxide particles. The thermal property of the polystyrene polymer material was then analyzed by the above-mentioned method for determining thermal stability and was compared with that of polystyrene polymer without titanium dioxide particles. The analysis result was shown in FIG. 2.

Example 2

Hydrolysis was carried out the same as Example 1 except changing the conditions into those set forth in the following Table 1 to obtain a monomer dispersion containing titanium dioxide particles. Namely, to a mixture of 10.0 g of styrene monomer and 2.5 g of titanium tetraisopropoxide, 1.06 g of acetic acid as the chelating agent (with the molar equivalent ratio of acetic acid to titanium tetraisopropoxide being 2) and 0.32 g of water (with the molar equivalent ratio of water to titanium tetraisopropoxide being 2) were added. The resultant mixture was stirred at a temperature of 25° C. to hydrolyze titanium tetraisopropoxide to give a clear solution which was a styrene monomer dispersion containing 5% by weight of titanium oxide. The particle size distribution of the titanium dioxide particles in the styrene monomer dispersion was measured with a DLS apparatus (Zetasizer nano ZS). The result was shown in Table 1.

Example 3

Figure 3:
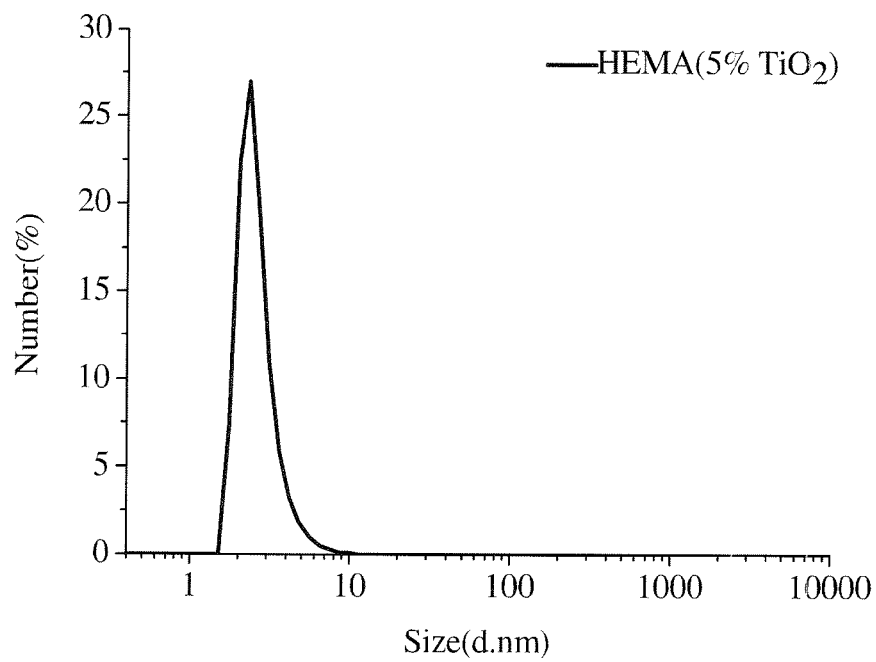
FIG. 3 is a graph showing the particle size distribution of the titanium dioxide nanoparticles dispersed in the monomer dispersion prepared in Example 3.
Figure 4:
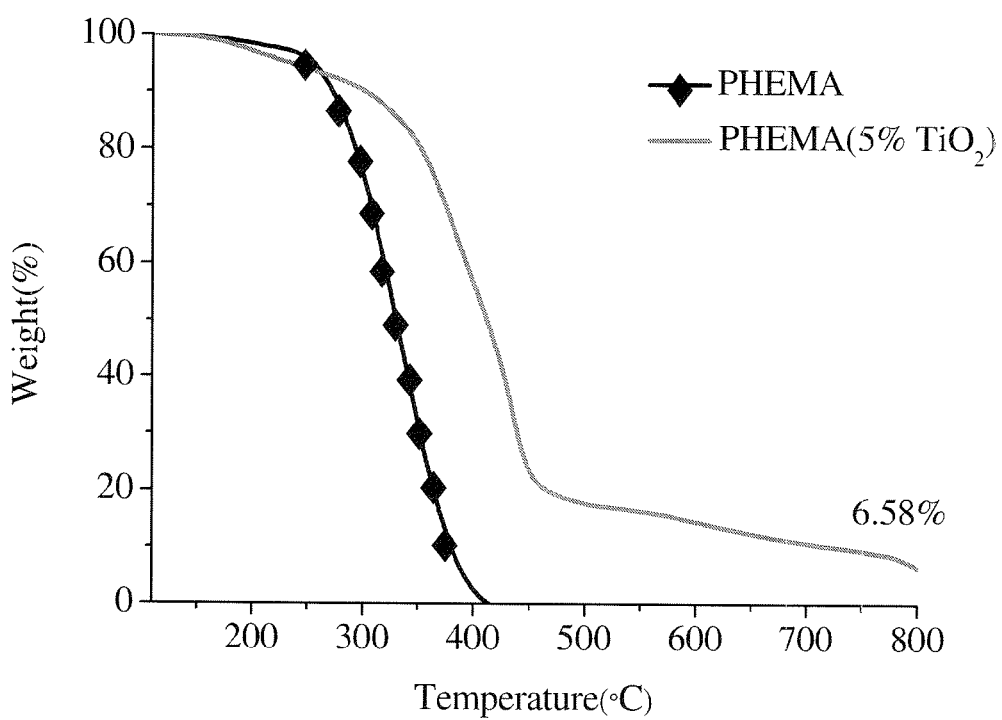
FIG. 4 is a graph showing the thermal analysis result of a polymer material prepared in Example 3, in which the polymer material is obtained by polymerizing the monomer dispersion containing titanium dioxide nanoparticles.

Hydrolysis was carried out the same as Example 1 except changing the conditions into those set forth in the Table 1 to obtain a monomer dispersion containing titanium dioxide particles. Namely, to a mixture of 5.3 g of 2-hydroxyethyl methacrylate monomer and 1.53 g of titanium tetraisopropoxide, 0.647 g of acetic acid as the chelating agent (with the molar equivalent ratio of acetic acid to titanium tetraisopropoxide being 2) and 0.2 g of water (with the molar equivalent ratio of water to titanium tetraisopropoxide being 2) were added. The resultant mixture was stirred at a temperature of 25° C. to hydrolyze titanium tetraisopropoxide to give a clear solution which was a 2-hydroxyethyl methacrylate monomer dispersion containing 5% by weight of titanium dioxide. The particle size distribution of the titanium dioxide particles in the 2-hydroxyethyl methacrylate monomer dispersion was measured with a DLS apparatus (Zetasizer nano ZS). The result was shown in Table 1 and FIG. 3. Similar to the Example 1, 0.02 g of azobisisobutyronitrile (as the polymerization initiator) was added into 2 g of the 2-hydroxyethyl methacrylate monomer dispersion containing 5% by weight of titanium dioxide particles, and thermopolymerization was performed at a temperature of 90° C. for 3 hours to obtain a poly(2-hydroxyethyl methacrylate) polymer material containing titanium dioxide particles. The thermal property of the poly(2-hydroxyethyl methacrylate) polymer material was then analyzed by the above-mentioned method for determining thermal stability and was compared with that of poly(2-hydroxyethyl methacrylate) polymer material without titanium dioxide particles. The analysis result was shown in FIG. 4.

Example 4

Figure 5:
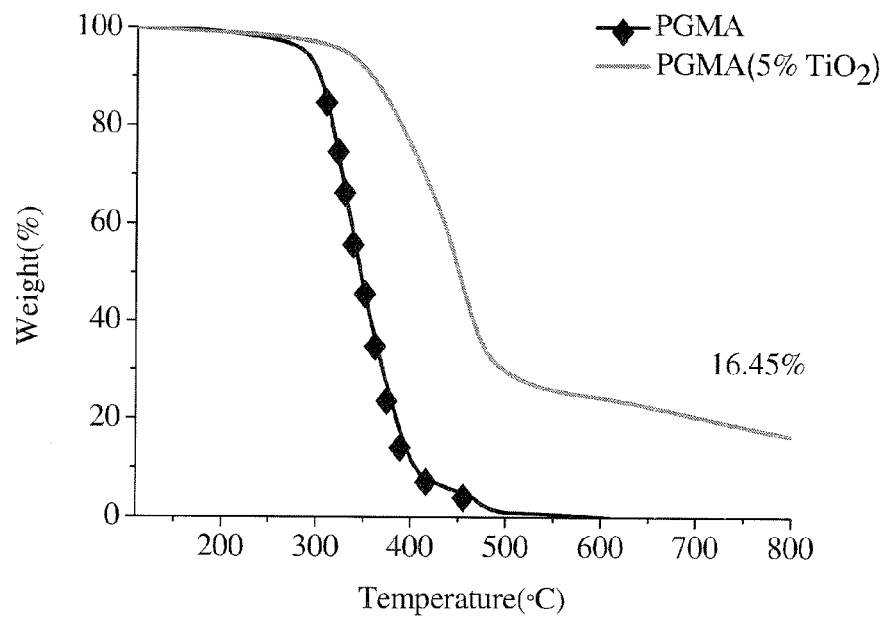
FIG. 5 is a graph showing the thermal analysis result of an organic-inorganic hybrid polymer material prepared in Example 4, in which the polymer material is obtained by polymerizing the monomer dispersion containing titanium dioxide nanoparticles.
Figure 6:
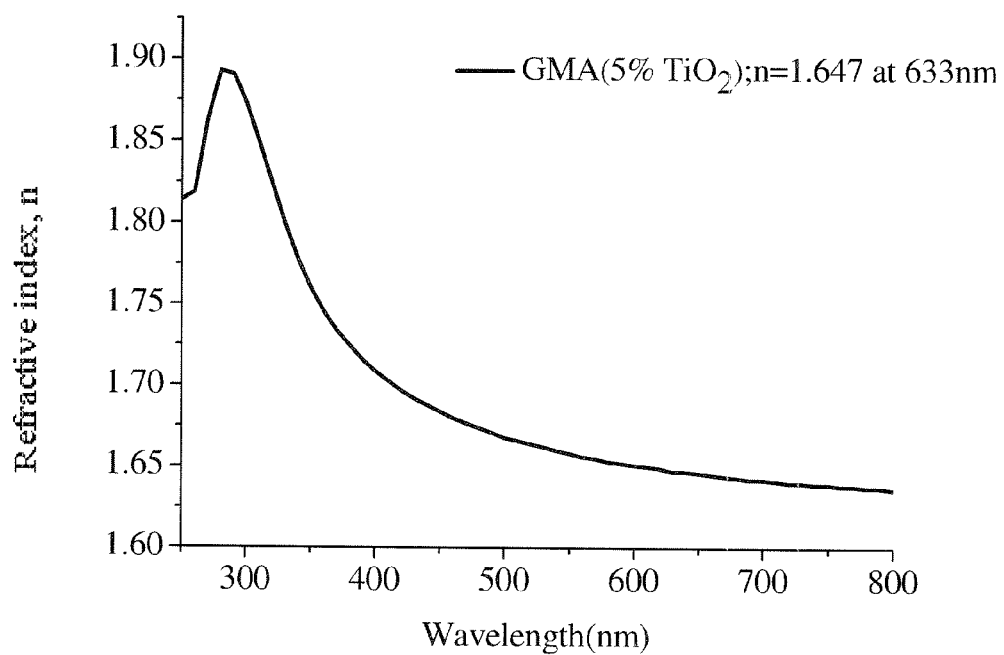
FIG. 6 is a graph showing the refractive index analysis result of a film prepared in Example 4, in which the film is formed by spin-coating the monomer dispersion containing titanium dioxide nanoparticles and then drying at room temperature.
Figure 7:
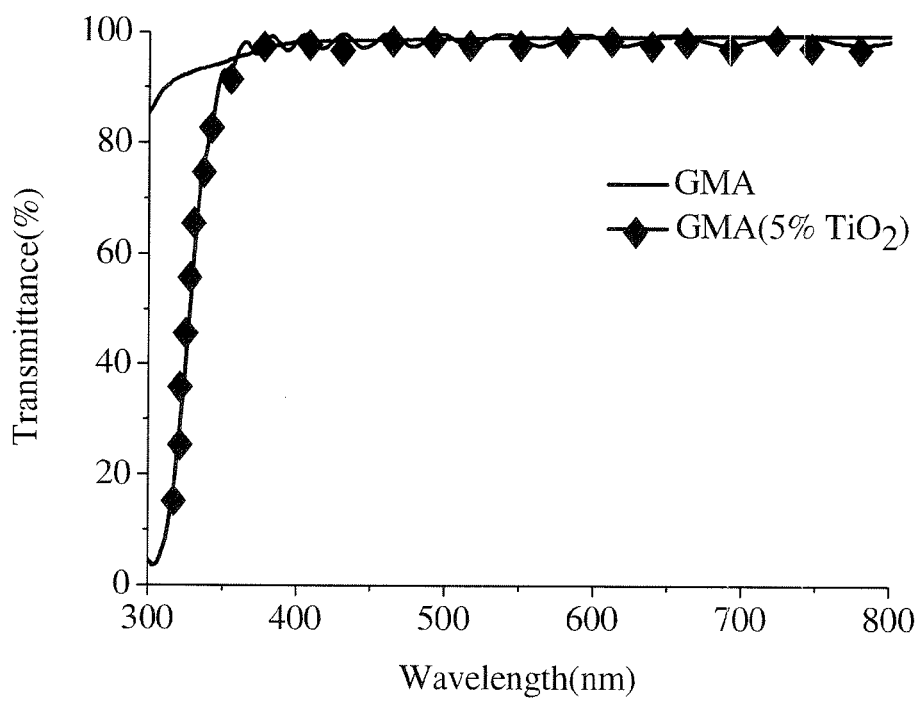
FIG. 7 is a graph showing the transmittance measurements of a film prepared in Example 4, in which the film is formed by spin-coating the monomer dispersion containing titanium dioxide nanoparticles and then drying at room temperature.

Hydrolysis was carried out the same as Example 1 except changing the conditions into those set forth in the Table 1 to obtain a monomer dispersion containing titanium dioxide particles. Namely, to a mixture of 5.3 g of glycidyl methacrylate monomer and 1.53 g of titanium tetraisopropoxide, 0.647 g of acetic acid as the chelating agent (with the molar equivalent ratio of acetic acid to titanium tetraisopropoxide being 2) and 0.2 g of water (with the molar equivalent ratio of water to titanium tetraisopropoxide being 2) were added. The resultant mixture was stirred at a temperature of 25° C. to hydrolyze titanium tetraisopropoxide to give a clear solution which was a glycidyl methacrylate monomer dispersion containing 5% by weight of titanium dioxide. The particle size distribution of the titanium dioxide particles in the glycidyl methacrylate monomer dispersion was measured with a DLS apparatus (Zetasizer nano ZS). The result was shown in Table 1. Similar to the Example 1, 0.02 g of azobisisobutyronitrile (as the polymerization initiator) was added into 2 g of the glycidyl methacrylate monomer dispersion containing 5% by weight of titanium dioxide particles, and thermopolymerization was performed at a temperature of 90° C. for 3 hours to obtain a poly(glycidyl methacrylate) polymer material containing titanium dioxide particles. The thermal property of the poly(glycidyl methacrylate) polymer material was then analyzed by the above-mentioned method for determining thermal stability, and the analysis result was shown in FIG. 5. In addition, 0.5 ml of the glycidyl methacrylate monomer dispersion containing 5% by weight of titanium dioxide particles was spin-coated on a glass substrate to form a film and dried at room temperature to obtain a transparent film of a high refractive index. The refractive index and transmittance of the high refractive optical film were analyzed using the above-mentioned methods, and the analysis results were shown in FIGS. 6 and 7, respectively. According to FIG. 6, the refractive index of the optical film was 1.647 at the wavelength of 633 nm.

Example 5

Hydrolysis was carried out the same as in the Example 1 except changing the conditions into those set forth in the Table 1 to obtain a monomer dispersion containing titanium dioxide particles. Namely, to a mixture of 5.3 g of glycidyl methacrylate monomer and 1.53 g of titanium tetraisopropoxide, 0.647 g of acetic acid as the chelating agent (with the molar equivalent ratio of acetic acid to titanium tetraisopropoxide being 2) and 0.2 g of water (with the molar equivalent ratio of water to titanium tetraisopropoxide being 2) were added. The resultant mixture was stirred at 4° C. to hydrolyze titanium tetraisopropoxide to give a clear solution which was a glycidyl methacrylate monomer dispersion containing 5% by weight of titanium dioxide. The particle size distribution of the titanium dioxide particles in the glycidyl methacrylate monomer dispersion was measured with a DLS apparatus (Zetasizer nano ZS). The result was shown in Table 1.

Example 6

Hydrolysis was carried out the same as the Example 1 except changing the conditions into those set forth in the Table 1 to obtain a monomer dispersion containing titanium dioxide particles. Namely, to a mixture of 5.3 g of methyl methacrylate monomer and 2.03 g of titanium tetraisopropoxide, 2.57 g of acetic acid as the chelating agent (with the molar equivalent ratio of acetic acid to titanium tetraisopropoxide being 6) and 0.26 g of water (with the molar equivalent ratio of water to titanium tetraisopropoxide being 2) were added. The resultant mixture was stirred at a temperature of 25° C. to hydrolyze titanium tetraisopropoxide to give a clear solution which was a methyl methacrylate monomer dispersion containing 5% by weight of titanium dioxide. The particle size distribution of the titanium dioxide particles in the methyl methacrylate monomer dispersion was measured with a DLS apparatus (Zetasizer nano ZS). The result was shown in Table 1.

Example 7

Hydrolysis was carried out the same as the Example 1 except changing the conditions into those set forth in the Table 1 to obtain a monomer dispersion containing titanium dioxide particles. Namely, to a mixture of 5.3 g of methyl methacrylate monomer and 1.75 g of titanium tetraisopropoxide, 1.5 g of acetic acid as the chelating agent (with the molar equivalent ratio of acetic acid to titanium tetraisopropoxide being 4) and 0.22 g of water (with the molar equivalent ratio of water to titanium tetraisopropoxide being 2) were added. The resultant mixture was stirred at a temperature of 25° C. to hydrolyze titanium tetraisopropoxide to give a clear solution which was a methyl methacrylate monomer dispersion containing 5% by weight of titanium dioxide. The particle size distribution of the titanium dioxide particles in the methyl methacrylate monomer dispersion was measured with a DLS apparatus (Zetasizer nano ZS). The result was shown in Table 1.

Example 8

Hydrolysis was carried out the same as the Example 1 except for changing the conditions into those set forth in the Table 1 to obtain a monomer dispersion containing titanium dioxide particles. Namely, to a mixture of 5.3 g of aniline monomer and 1.53 g of titanium tetraisopropoxide, 0.647 g of acetic acid as the chelating agent (with the molar equivalent ratio of acetic acid to titanium tetraisopropoxide being 2) and 0.2 g of water (with the molar equivalent ratio of water to titanium tetraisopropoxide being 2) were added. The resultant mixture was stirred at 25° C. to hydrolyze titanium tetraisopropoxide to give a clear solution which was an aniline monomer dispersion containing 5% by weight of titanium dioxide. The particle size distribution of the titanium dioxide particles in the aniline monomer dispersion was measured with a DLS apparatus (Zetasizer nano ZS). The result was shown in Table 1.

Example 9

Hydrolysis was carried out the same as the Example 1 except changing the conditions into those set forth in the Table 1 to obtain a monomer dispersion containing titanium dioxide particles. Namely, to a mixture of 5.3 g of aniline monomer and 4.6 g of titanium tetraisopropoxide, 1.94 g of acetic acid as the chelating agent (with the molar equivalent ratio of acetic acid to titanium tetraisopropoxide being 2) and 0.58 g of water (with the molar equivalent ratio of water to titanium tetraisopropoxide being 2) were added. The resultant mixture was stirred at a temperature of 25° C. to hydrolyze titanium tetraisopropoxide to give a clear solution which was an aniline monomer dispersion containing 10% by weight of titanium dioxide. The particle size distribution of the titanium dioxide particles in the aniline monomer dispersion was measured with a DLS apparatus (Zetasizer nano ZS). The result was shown in Table 1. Moreover, in 2.95 g methanol as a solvent, 150 μL of the aniline monomer dispersion containing titanium dioxide particles was added along with 1.95 g of iron (III) p-toluenesulfonate hexahydrate as the initiator and mixed. The mixture was spin-coated on a glass substrate and subjected to polymerization at a temperature of 110° C. for 20 minutes. The film thus formed was subjected to the above-mentioned electrical conductivity measurement, and found being 10.22 (S/cm). A film made from a polyaniline material containing no titanium dioxide particles was subjected to the same electrical conductivity measurement, and found being 8.63 (S/cm).

Example 10

Hydrolysis was carried out the same as the Example 1 except changing the conditions into those set forth in the Table 1 to obtain a monomer dispersion containing titanium dioxide particles. Namely, to a mixture of 5.3 g of ethylene glycol monomer and 0.2 g of titanium tetraisopropoxide, 0.084 g of acetic acid as the chelating agent (with the molar equivalent ratio of acetic acid to titanium tetraisopropoxide being 2) and 0.025 g of water (with the molar equivalent ratio of water to titanium tetraisopropoxide being 2) were added. The resultant mixture was stirred at a temperature of 25° C. to hydrolyze titanium tetraisopropoxide to give a clear solution which was an ethylene glycol monomer dispersion containing 5% by weight of titanium dioxide. The particle size distribution of the titanium dioxide particles in the ethylene glycol monomer dispersion was measured with a DLS apparatus (Zetasizer nano ZS). The result was shown in Table 1.

Example 11

Figure 8:
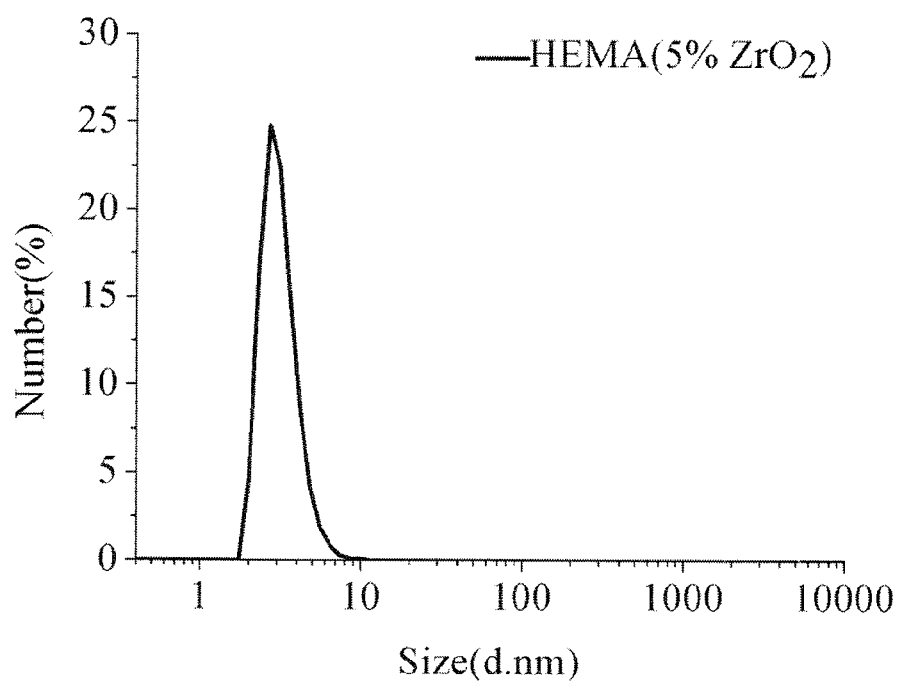
FIG. 8 is a graph showing the particle size distribution of the zirconium dioxide nanoparticles dispersed in the monomer dispersion prepared in Example 11.
Figure 9:
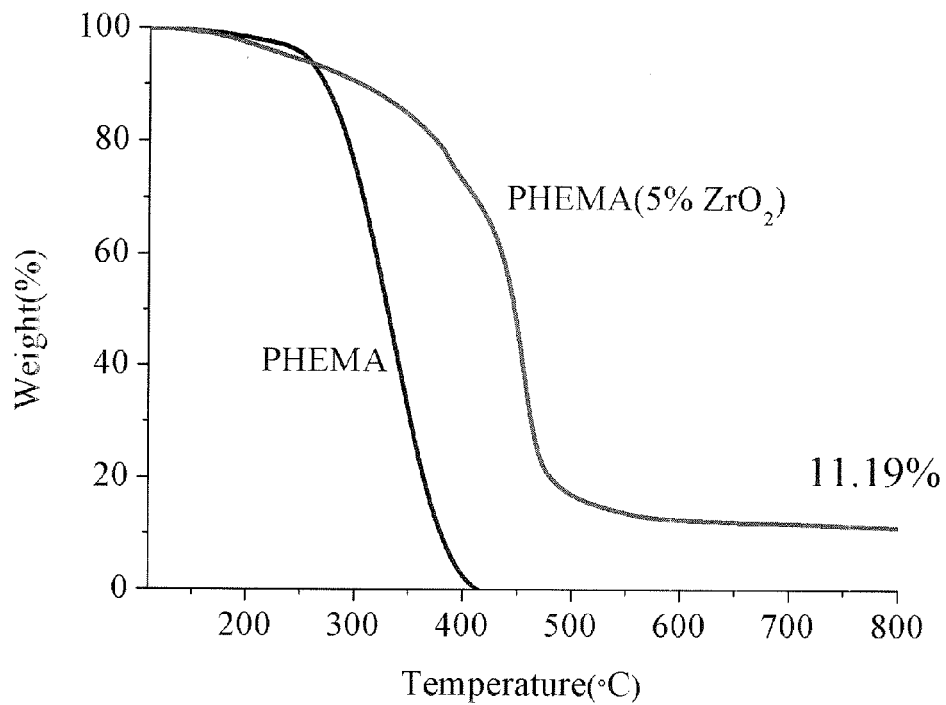
FIG. 9 is a plot showing the thermal analysis result of an organic-inorganic hybrid polymer material prepared in Example 11, in which the polymer material is obtained by polymerizing the monomer dispersion containing zirconium dioxide nanoparticles.
Figure 10:
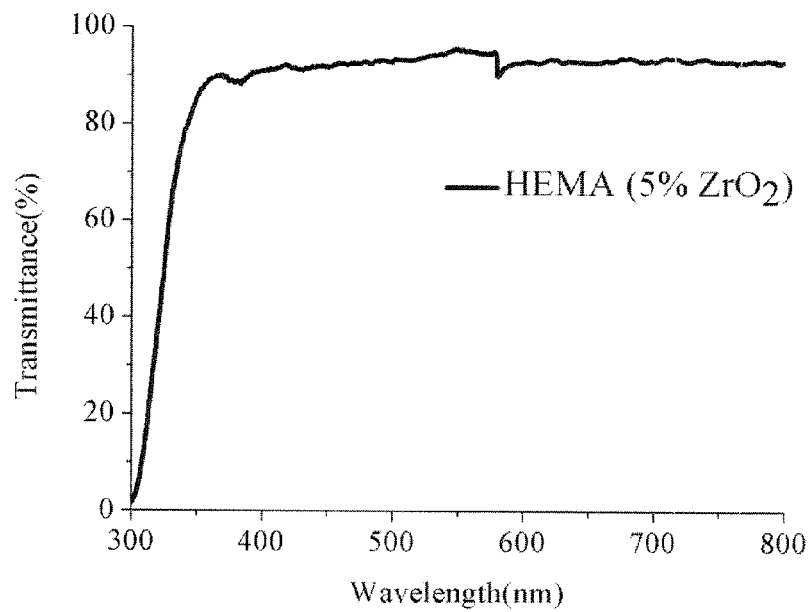
FIG. 10 is a graph showing the transmittance of a film prepared in Example 11, in which the film is formed by spin-coating drying the monomer dispersion containing zirconium dioxide nanoparticles and then drying at room temperature.

Hydrolysis was carried out the same as the Example 1 except changing the conditions into those set forth in the Table 1 to obtain a monomer dispersion containing zirconium dioxide particles. Namely, to a mixture of 5.3 g of 2-hydroxyethyl methacrylate monomer and 0.95 g of zirconium tetrapropoxide, 0.35 g of acetic acid as the chelating agent (with the molar equivalent ratio of acetic acid to zirconium tetrapropoxide being 2) and 0.104 g of water (with the molar equivalent ratio of water to zirconium tetrapropoxide being 2) were added. The resultant mixture was stirred at a temperature of 25° C. to hydrolyze zirconium tetrapropoxide to give a clear solution which was a 2-hydroxyethyl methacrylate monomer dispersion containing 5% by weight of zirconium dioxide. The particle size distribution of the zirconium dioxide particles in the 2-hydroxyethyl methacrylate monomer dispersion was measured with a DLS apparatus (Zetasizer nano ZS). The result was shown in Table 1 and FIG. 8. Similar to the Example 1, 0.02 g of azobisisobutyronitrile (as the polymerization initiator) was added into 2 g of the 2-hydroxyethyl methacrylate monomer dispersion containing 5% by weight of zirconium dioxide particles, and thermopolymerization was performed at a temperature of 90° C. for 3 hours to obtain a poly(2-hydroxyethyl methacrylate) polymer material containing zirconium dioxide particles. The thermal property of the poly(2-hydroxyethyl methacrylate) polymer material was then analyzed by the above-mentioned method for determining thermal stability, and the analysis result was shown in FIG. 9. In addition, 0.5 ml of the 2-hydroxyethyl methacrylate monomer dispersion containing 5% by weight of zirconium dioxide particles was spin-coated on a glass substrate to form a film and dried at room temperature to obtain a transparent film with high refractive index. The transmittance of the high refractive optical film was analyzed using the above-mentioned method, and the analysis result is plotted in FIG. 10. From FIG. 10, it is found that the transmittance of the optical film was 91.02% at a wavelength of 400 nm.

Example 12

Figure 11:
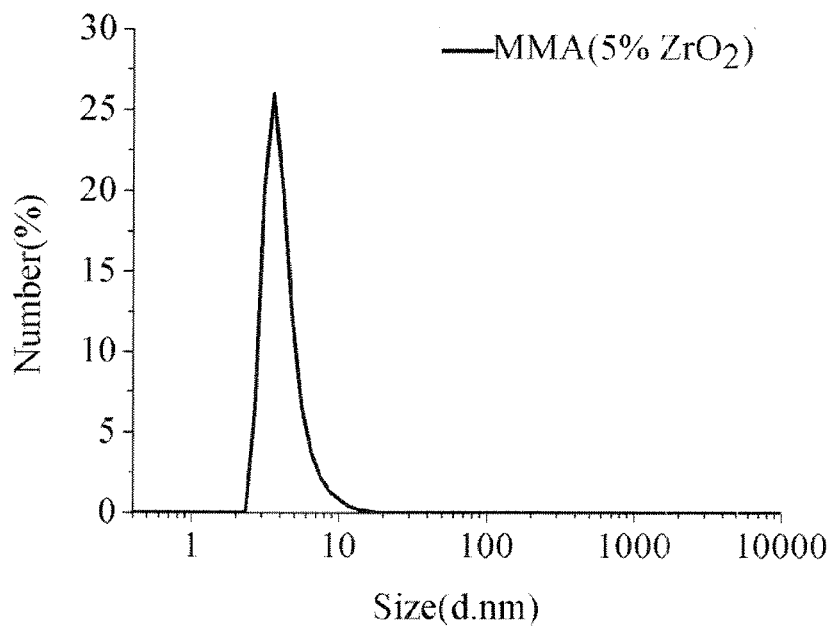
FIG. 11 is a graph showing the particle size distribution of the zirconium dioxide nanoparticles dispersed in the monomer dispersion prepared in Example 12.
Figure 12:
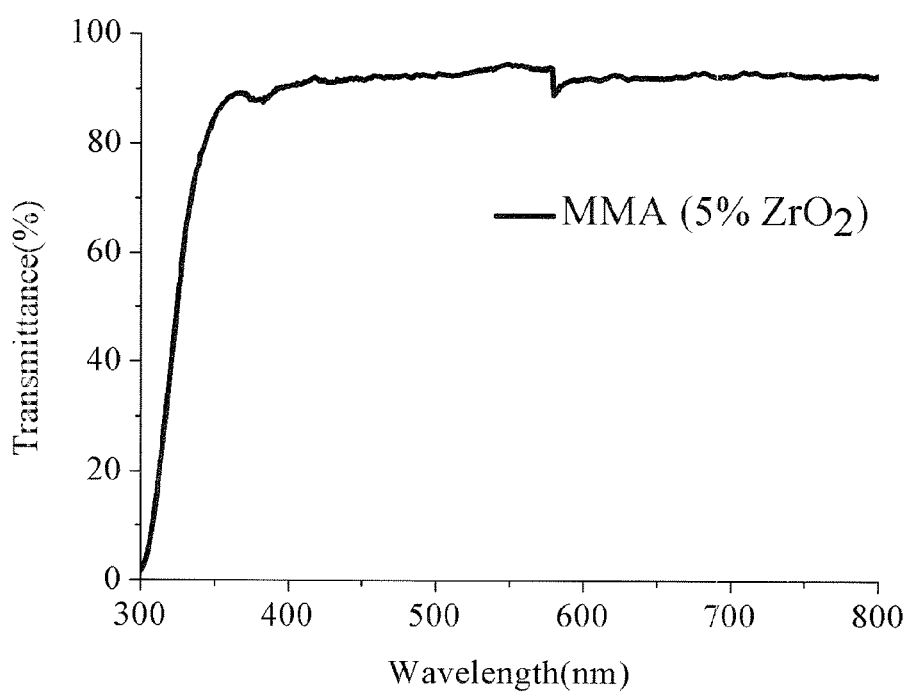
FIG. 12 is a graph showing the transmittance of a film prepared in Example 12, in which the film is formed by spin-coating drying the monomer dispersion containing zirconium dioxide nanoparticles and drying at room temperature.

Hydrolysis was carried out the same as the Example 1 except changing the conditions into those set forth in the Table 1 to obtain a monomer dispersion containing zirconium dioxide particles. Namely, to a mixture of 5.3 g of methyl methacrylate monomer and 0.95 g of zirconium tetrapropoxide, 0.7 g of acetic acid as the chelating agent (with the molar equivalent ratio of acetic acid to zirconium tetrapropoxide being 4) and 0.104 g of water (with the molar equivalent ratio of water to zirconium tetrapropoxide being 2) were added. The resultant mixture was stirred at a temperature of 25° C. to hydrolyze zirconium tetrapropoxide to give a clear solution which was a methyl methacrylate monomer dispersion containing 5% by weight of zirconium dioxide. The particle size distribution of the zirconium dioxide particles in the methyl methacrylate monomer dispersion was measured with a DLS apparatus (Zetasizer nano ZS). The result was shown in Table 1 and FIG. 11. In addition, 0.5 ml of the methyl methacrylate monomer dispersion containing 5% by weight of zirconium dioxide particles was spin-coated on a glass substrate to form a film and dried at room temperature to obtain a transparent film with high refractive index. The transmittance of the high refractive optical film was analyzed using the above-mentioned method, and the analysis result is shown in FIG. 12. From FIG. 12 it is found that the transmittance of the optical film was 90.52% at a wavelength of 400 nm.

Example 13

Hydrolysis was carried out the same as the Example 1 except changing the conditions into those set forth in the Table 1 to obtain a monomer dispersion containing zirconium dioxide particles. Namely, to a mixture of 5.3 g of aniline monomer and 1.53 g of zirconium tetrapropoxide, 0.56 g of acetic acid as the chelating agent (with the molar equivalent ratio of acetic acid to zirconium tetrapropoxide being 2) and 0.168 g of water (with the molar equivalent ratio of water to zirconium tetrapropoxide being 2) were added. The resultant mixture was stirred at 25° C. to hydrolyze zirconium tetrapropoxide to give a clear solution which was an aniline monomer dispersion containing 5% by weight of zirconium dioxide. The particle size distribution of the zirconium dioxide particles in the aniline monomer dispersion was measured with a DLS apparatus (Zetasizer nano ZS). The result was shown in Table 1 and FIG. 11.

TABLE 1

| | Monomer type | Monomer weight (g) | Equivalent ratio of acetic acid*[1] | Equivalent ratio of water*[1] | Weight of alkoxide*[7] (g) | Reaction temperature (° C.) | Content of inorganic particles in dispersion (%) | Particle size distribution of inorganic particles (nm) |
|---|---|---|---|---|---|---|---|---|
| Example 1 | Styrene | 5.3 | 2 | 2 | 1.53 | 25 | 5 | 2.0~9.0 |
| Example 2 | Styrene | 10.0 | 2 | 2 | 2.5 | 25 | 5 | 3.0~10.0 |
| Example 3 | HEMA*[2] | 5.3 | 2 | 2 | 1.53 | 25 | 5 | 1.5~9.0 |
| Example 4 | GMA*[3] | 5.3 | 2 | 2 | 1.53 | 25 | 5 | 10.5~70.0 |
| Example 5 | GMA*[3] | 5.3 | 2 | 2 | 1.53 | 4 | 5 | 10.5~70.0 |
| Example 6 | MAA*[4] | 5.3 | 10 | 2 | 3 | 25 | 5 | 1.5~6.0 |
| Example 7 | MMA*[5] | 5.3 | 4 | 2 | 1.75 | 25 | 5 | 2.0~10.0 |
| Example 8 | Aniline | 5.3 | 2 | 2 | 1.53 | 25 | 5 | 0.5~1.0 |
| Example 9 | Aniline | 5.3 | 2 | 2 | 4.6 | 25 | 10 | 1.5~6.0 |
| Example 10 | EG*[6] | 5.3 | 2 | 2 | 1.53 | 25 | 5 | 1.0~4.0 |
| Example 11 | HEMA*[2] | 5.3 | 2 | 2 | 0.95 | 25 | 5 | 1.0~10.0 |
| Example 12 | MMA*[5] | 5.3 | 4 | 2 | 0.95 | 25 | 5 | 2.0~9.0 |
| Example 13 | Aniline | 5.3 | 2 | 2 | 1.53 | 25 | 5 | 1.0~6.0 |

Notes:
*[1]Molar equivalent ratio relative to alkoxide
*[2]HEMA: 2-hydroxyethyl methacrylate
*[3]GMA: glycidyl methacrylate
*[4]MAA: methacrylic acid
*[5]MMA: methyl methacrylate
*[6]EG: ethylene glycol
*[7]Kinds of the alkoxide is titanium tetraisopropoxide in Examples 1~10 and zirconium tetrapropoxide in Examples 11~13

From the above results, it is known that the process of the present invention can produce a dispersion in which inorganic oxide particles with high refractive index are stably dispersed in a monomer. Thus, inorganic oxide particles can be directly synthesized in a monomer for which is selected depending on the end purpose or use, without having to prepare an inorganic oxide gel and then polymerize the gel with the desired monomer as is required in the prior art. By using a polymerization initiator, the inorganic oxide particle-containing monomer dispersion of the present invention can be polymerized to form an organic-inorganic hybrid polymer material exhibiting excellent thermal properties, and a film made from the polymer material exhibits high transparent and refractive index and thus is suitable used in optical devices, such as optical waveguides. Moreover, when an electrically conductive monomer is used as the media in the inorganic oxide particle-containing monomer dispersion of the present invention, the dispersion can be formed into a film exhibiting not only electrical conductivity but also excellent thermal properties, high transparency, high refractive index, and hence increase its application.

What is claimed is:

1. A process for preparing a stabilized monomer dispersion containing inorganic oxide nanoparticles with a high refractive index greater than 1.65, the process comprising the steps of:
condensing and then hydrolyzing an alkoxide precursor corresponding to the inorganic oxide in a reactive monomer serving as a solvent in the presence of an chelating agent and water at a temperature of from 0 to 50° C. to produce a dispersion consisting of the monomer and inorganic oxide nanoparticles dispersed therein, wherein an equivalent ratio of the water to the alkoxide is equal to or less than 3, and an equivalent ratio of the chelating agent to the alkoxide is at least 2.

2. The process of claim 1, wherein the inorganic oxide nanoparticles are selected from the group consisting of titanium dioxide, zirconium dioxide, and cerium dioxide.

3. The process of claim 1, wherein the alkoxide precursor is represented by $X(OR)_4$, wherein R's are the same or different and represent a straight or branched alkyl group having 1 to 8 carbon atoms, and X is Ti, Zr, or Ce.

4. The process of claim 3, wherein the alkoxide is titanium tetraisopropoxide or titanium tetrabutoxide.

5. The process of claim 3, wherein the alkoxide is zirconium tetraethoxide or zirconium tetrapropoxide.

6. The process of claim 1, wherein the chelating agent is a compound having a carboxyl (—COON) functional group.

7. The process of claim 6, wherein the chelating agent is acetic acid, citric acid, acrylic acid, or methacrylic acid.

* * * * *